July 1, 1947. A. MORITZ Plant Pat. 741
PEAR TREE
Filed March 8, 1946
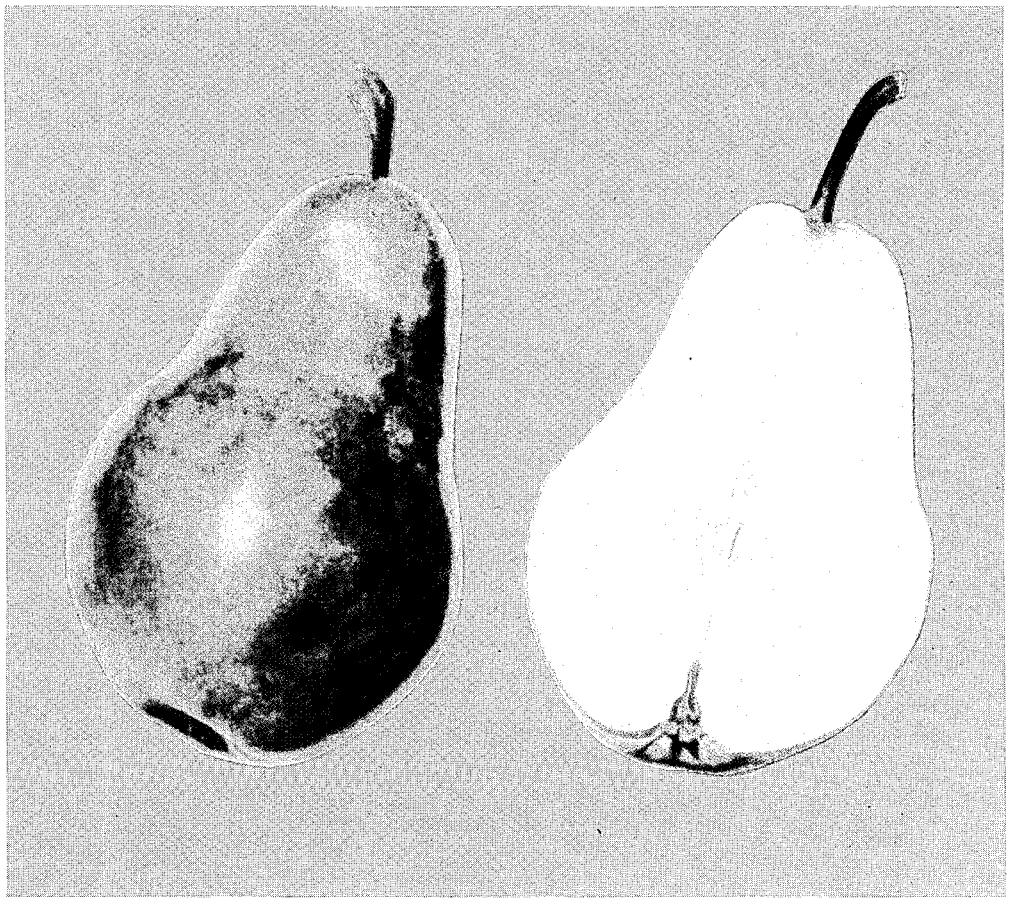
Inventor
Arthur Moritz
By Robert Cobb
Attorneys Patented July 1, 1947

Plant Pat. 741

UNITED STATES PATENT OFFICE

741

PEAR TREE

Arthur Moritz, Zillah, Wash., assignor to Arthur D. MacKelvie, Zillah, Wash.

Application March 8, 1946, Serial No. 653,069

1 Claim. (Cl. 47—62)

The present discovery relates to a new and distinct variety of pear tree, originating as a limb sport of the well-known Bartlett variety.

This new variety, while maturing at the same period as its parent and having much the same growing habits as the parent variety, distinctively differs therefrom primarily in the coloring of the fruit. Whereas the fruit of the Bartlett variety is green during the growing season and at maturing or harvesting season turns yellow, this new sport during growing season and harvest is all-over Mahogany Red, over a somewhat indistinct stripe undercoloring.

In minor particulars, the new variety is further distinguishable from the normal Bartlett variety, i. e. the texture of the fruit is a little finer, the quality somewhat sweeter, and the wood reddish in color.

In the accompanying drawing, there are depicted a view in elevation and a sectional view of specimens of the new variety fruit, the coloring thereof being as near as can be represented in illustration. Because of the unique coloring and improved qualities, this new variety finds a ready demand on the market.

Asexual reproduction shows that the characteristics hold true through succeeding propagations.

The following is a detailed description of the new variety, color terminology according with ordinary dictionary definition, except where indicated to be according to Maerz & Paul Dictionary of Colors:

Tree: Medium size; vigorous; upright; tall; rapid growing; hardy; very productive; regular bearer.

*Trunk.*—Stocky; smooth.

*Branches.*—Thick; smooth; medium branching; reddish brown. *Lenticels*—medium number; small size.

*Leaves.*—Length, 3 inches. Width, 2 inches. Medium size; medium width; medium length; oval shape; taper-pointed; medium thick; dark green; smooth. *Margin*—finely serrate. *Petiole*—medium length; medium thick.

*Flowers.*—From accurate records kept for growing tests at Wapato, Washington, and accepted by the Washington State College and the Extension Service as being accurate, the following dates of full bloom and date of harvest over a period of years are given as follows:

| Year | Full Bloom | Harvest |
|---|---|---|
| 1941 | April 2 | August 6. |
| 1942 | April 10 | August 10. |
| 1943 | April 14 | August 16. |
| 1944 | No record | |
| 1945 | April 19 | August 10. |
| 1946 | April 14 | August 6. |

The dates of full bloom are the dates when this orchard was in prime blooming condition, or the maximum number of blooms out. The first blooms would show up some two or three days earlier. The date of harvest is a record when the pear was in prime condition for canning and the green fruit market. Dates of first and full bloom—about April 1 to 20, at Wapato, Washington. Medium late compared with other varieties. Medium size; white.

Fruit: Maturity when described—date of first and last picking, hard ripe, August 5 to 10, on the average eating ripe approximately nine days later and when picked and placed in common storage. When placed in cold storage, the pears were in perfect condition (1945 season) on December 1. All Bartlett variety pears, kept under like conditions, had begun to deteriorate and show black centers with one exception.

*Size.*—Axial diameter—3½ inches; transverse—2½ inches.

*Form.*—Oblong; obtuse; pyriform. *Cavity*—small; lipped; acute. *Basin*—narrowly furrowed and shallow. *Stem*—long; often curved; thick. *Calyx*—open; segments persistent; narrowly acute. Outer surface and inner surface—glabrous. *Eye*—large.

*Skin.*—Thin; tender; smooth. *Dots*—conspicuous; many; small; ruptured, oblong. *Color of dots*—russeted. *Distribution of dots*—numerous. *Ground color*—straw. *Color markings*—splashed. *Color of markings* — Mahogany Red. *Bloom* — scant. *General color effect*—Mahogany Red.

More specifically describing the color of this fruit according to a Standard Color Chart, the following is given from data compiled by an authority of the State College of Washington, Pullman, Washington. At soft ripe prime eating maturity the dominant color is "Holly Berry" Red, as given in Maerz & Paul, a Dictionary of Colors, 1st Edition, 1930, Plate 4, page 30.

When hard ripe (picking time) the dominant color is "Morocco Red," Plate 6, page 34.

*Flesh*—Juicy. *Color of flesh*—White. *Texture*—Fine (noticeably finer grain than Bartlett variety; melting. *Flavor*—delicate; aroma distinct. Sugar content of this variety ten points higher than the Bartlett variety.

*Core.*—*Bundle area* (longitudinal section)—large. *Core lines*—clasping, in cross section distinct. *Carpellary area*—distinct; large. *Calyx tube*—funnel. *Stem of funnel*—long. *Styles*—wanting. *Axillary cavity*—wanting. *Seed cells*—closed.

*Seeds.*—Medium in size and length; plump; acute. *Color*—Brown.

Use: Local; dessert; culinary.

Keeping quality: Medium.

Resistance to: Insects—medium.

I claim:

A new and distinct variety of pear tree, characterized as to novelty dominantly by the all-over Mahogany Red coloring of the fruit, improved keeping quality, noticeably finer grain and higher sugar content, as compared with its parent variety, while retaining the latter's habits of growth and maturity season, substantially as shown and described.

ARTHUR MORITZ.